United States Patent
Arai et al.

(10) Patent No.: US 8,927,777 B2
(45) Date of Patent: Jan. 6, 2015

(54) METHOD OF PRODUCING 1-(2-T-BUTYL CYCLOHEXYLOXY)-2-ALKANOL

(71) Applicant: Kao Corporation, Chuo-ku (JP)

(72) Inventors: Tsubasa Arai, Wakayama (JP); Shinji Kotachi, Wakayama (JP); Yoshiharu Ataka, Wakayama (JP)

(73) Assignee: Kao Corporation, Chuo-ku (JP)

( * ) Notice: Subject to any disclaimer, the term of this patent is extended or adjusted under 35 U.S.C. 154(b) by 0 days.

(21) Appl. No.: 14/368,428

(22) PCT Filed: Dec. 25, 2012

(86) PCT No.: PCT/JP2012/083456
§ 371 (c)(1),
(2) Date: Jun. 24, 2014

(87) PCT Pub. No.: WO2013/099859
PCT Pub. Date: Jul. 4, 2013

(65) Prior Publication Data
US 2014/0350306 A1    Nov. 27, 2014

(30) Foreign Application Priority Data
Dec. 26, 2011 (JP) ................................. 2011-284417

(51) Int. Cl.
C07C 41/20    (2006.01)
(52) U.S. Cl.
CPC ...................................... *C07C 41/20* (2013.01)
USPC ........................................................ 568/579
(58) Field of Classification Search
CPC ...................................................... C07C 41/20
USPC ........................................................ 568/579
See application file for complete search history.

(56) References Cited

U.S. PATENT DOCUMENTS

| | | | |
|---|---|---|---|
| 5,194,423 A | 3/1993 | Koshino et al. | |
| 5,446,208 A | 8/1995 | Koshino et al. | |

FOREIGN PATENT DOCUMENTS

| | | |
|---|---|---|
| JP | 4 217937 | 8/1992 |
| JP | 4 327553 | 11/1992 |
| JP | 5 339188 | 12/1993 |
| JP | 6 263677 | 9/1994 |
| JP | 2013 151481 | 8/2013 |

OTHER PUBLICATIONS

U.S. Appl. No. 14/368,381, filed Jun. 24, 2014, Arai, et al.
Margot, C., et al., "Amber-Woody Scent: Alcohols with Divergent Structure Present Common Olfactory Characteristics and Sharp Enantiomer Differentiation", Helvetica Chimica Acta, vol. 87, No. 10, pp. 2662-2684, (2004).
International Search Report Issued Mar. 12, 2013 in PCT/JP12/083456 Filed Dec. 25, 2012.

*Primary Examiner* — Brian J Davis
(74) *Attorney, Agent, or Firm* — Oblon, Spivak, McClelland, Maier & Neustadt, L.L.P.

(57) ABSTRACT

The present invention relates to [1] a method of producing a 1-(2-t-butylcyclohexyloxy)-2-alkanol including a step of adjusting a raw material mixture containing a 1-(2-t-butylphenyloxy)-2-alkanol represented by the formula (1) to a pH of from 7.5 to 10.0 and hydrogenating it in the presence of a palladium catalyst (A) and a metal catalyst (B) containing one or more kinds of members selected from ruthenium, rhodium, platinum, and nickel; and [2] a perfume composition containing a 1-(2-t-butylcyclohexyloxy)-2-alkanol obtained by the foregoing method. The present invention provides a method of efficiently producing a 1-(2-t-butylcyclohexyloxy)-2-alkanol having a high trans-isomer content and a strong woody or amber-like fragrance as a perfume material and also having excellent persistence of aroma.

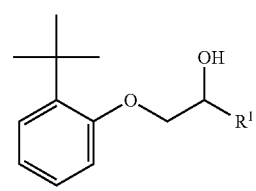

(1)

(In the formula, $R^1$ is a methyl group or an ethyl group.)

20 Claims, No Drawings

METHOD OF PRODUCING 1-(2-T-BUTYL CYCLOHEXYLOXY)-2-ALKANOL

TECHNICAL FIELD

The present invention relates to a method of producing a 1-(2-t-butylcyclohexyloxy)-2-alkanol.

BACKGROUND ART

An α-(2-alkylcyclohexyloxy)-β-alkanol, especially a 1-(2-t-butylcyclohexyloxy)-2-alkanol, is a useful perfume material having a woody or amber-like fragrance and excellent persistence of aroma and capable of being inexpensively produced. For that reason, investigations regarding an efficient production method thereof are made.

For example, PTL 1 discloses (1) a method of converting a 2-alkylcyclohexanol by using a strong base into an alcoholate, which is then allowed to react with an epoxide; and (2) a method of allowing a 2-alkylphenol to react with an epoxide in the presence of a base catalyst, thereby forming an α-(2-alkylphenyloxy)-β-alkanol, which is then hydrogenated in the presence of a metal catalyst.

PTL2 discloses a method of producing hydrogenating an α-(2-alkylphenyloxy)-β-alkanol in the presence of a catalyst containing (a) a palladium catalyst and (b) one or more kinds of metal catalysts selected from ruthenium, rhodium, platinum, and nickel for the purpose of obtaining an α-(2-alkylcyclohexyloxy)-β-alkanol having an excellent fragrance and a high trans-isomer content in a high yield within a short period of time.

In addition, PTL3 discloses a method of producing an ether alcohol of subjecting a cyclic ketal to hydrogenolysis in the presence of a catalyst containing 50% by weight or more of palladium and less than 50% by weight of one or more kinds of members selected from ruthenium, rhodium, platinum, and nickel.

CITATION LIST

Patent Literature

PTL 1: JP-A-4-217937
PTL 2: JP-A-4-327553
PTL 3: JP-A-6-263677

SUMMARY OF INVENTION

The present invention is concerned with the following [1] and [2].
[1] A method of producing a 1-(2-t-butylcyclohexyloxy)-2-alkanol including a step of adjusting a raw material mixture containing a 1-(2-t-butylphenyloxy)-2-alkanol represented by the formula (1) to a pH of from 7.5 to 10.0 and hydrogenating it in the presence of a palladium catalyst (A) and a metal catalyst (B) containing one or more kinds of members selected from ruthenium, rhodium, platinum, and nickel.

[Chem. 1]

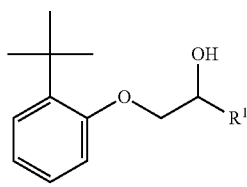

(1)

(In the formula, R is a methyl group or an ethyl group.)

[2] A perfume composition containing a 1-(2-t-butylcyclohexyloxy)-2-alkanol obtained by the method as set forth above in [1].

DESCRIPTION OF EMBODIMENTS

As described in PTLs 1 and 2, as for an α-(2-alkylcyclohexyloxy)-β-alkanol, especially a 1-(2-t-butylcyclohexyloxy)-2-alkanol, a trans-isomer thereof has an excellent fragrance. However, according to the methods disclosed in PTLs 1 and 2, the trans-isomer content of the obtained compound is not sufficiently satisfactory. For that reason, it is desirable to develop a method of producing an α-(2-alkylcyclohexyloxy)-β-alkanol having a high trans-isomer content and a strong fragrance and also having excellent persistence of aroma.

The present invention relates to a method of efficiently producing a 1-(2-t-butylcyclohexyloxy)-2-alkanol having a high trans-isomer content and a strong woody or amber-like fragrance as a perfume material and also having excellent persistence of aroma.

The present inventors have found that the above-described problem can be solved by a method of efficiently producing a 1-(2-t-butylcyclohexyloxy)-2-alkanol having a high trans-isomer content by adjusting a pH of a raw material mixture to a specified range and hydrogenating it in the presence of a palladium catalyst and a specified metal catalyst.

Specifically, the present invention is concerned with the following [1] and [2].
[1] A method of producing a 1-(2-t-butylcyclohexyloxy)-2-alkanol including a step of adjusting a raw material mixture containing a 1-(2-t-butylphenyloxy)-2-alkanol represented by the formula (1) to a pH of from 7.5 to 10.0 and hydrogenating it in the presence of a palladium catalyst (A) and a metal catalyst (B) containing one or more kinds of members selected from ruthenium, rhodium, platinum, and nickel.

[Chem. 2]

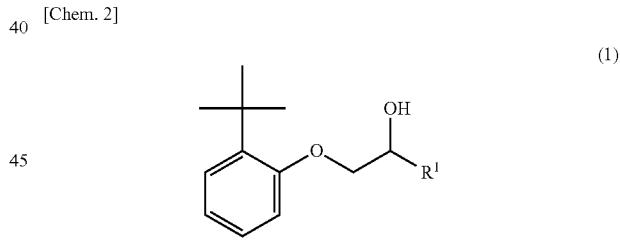

(1)

(In the formula, $R^1$ is a methyl group or an ethyl group.)
[2] A perfume composition containing a 1-(2-t-butylcyclohexyloxy)-2-alkanol obtained by the method as set forth above in [1].

According to the present invention, a method of efficiently producing a 1-(2-t-butylcyclohexyloxy)-2-alkanol having a high trans-isomer content and a strong woody or amber-like fragrance as a perfume material and also having very excellent persistence of aroma can be provided.

Production method of 1-(2-t-butylcyclohexyloxy)-2-alkanol

The method of producing a 1-(2-t-butylcyclohexyloxy)-2-alkanol of the present invention includes a step of adjusting a raw material mixture containing a 1-(2-t-butylphenyloxy)-2-alkanol represented by the formula (1) to a pH of from 7.5 to 10.0 and hydrogenating it in the presence of a palladium catalyst (A) and a metal catalyst (B) containing one or more kinds of members selected from ruthenium, rhodium, platinum, and nickel.

[Chem. 3]

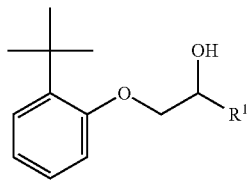

(1)

In the formula, R' is a methyl group or an ethyl group, and from the viewpoint as a perfume material, R' is more preferably an ethyl group. That is, 1-(2-t-butylcyclohexyloxy)-2-butanol is more preferable in terms of amber-like fragrance notes than 1-(2-t-butylcyclohexyloxy)-2-propanol and is particularly excellent as a perfume material in view of the fact that it has sweetness and volume in its fragrance.

<Palladium Catalyst (A)>

In the present invention, the palladium catalyst (A) is used in the hydrogenation step.

The palladium catalyst (A) is preferably a supported catalyst supported on a carrier. The carrier is preferably an inorganic carrier. Examples of the inorganic carrier include one or more kinds of carriers selected from active carbon, alumina, silica, silica magnesia, and zeolite. Of these, active carbon is more preferable from the viewpoint of catalytic activity.

Examples of the active carbon include active carbons derived from peat, bituminous coal, anthracite coal, lignite, wood, coconut shell, or the like. Of these, peat-derived active carbon is more preferable.

In the case where the palladium catalyst (A) is a supported catalyst, the palladium catalyst (A) refers to the whole including palladium and the carrier.

(Production of Active Carbon)

The active carbon can be, for example, obtained by carbonizing a carbon material produced in the usual way, activating it by a known method, and dipping the resultant in a dilute hydrochloric acid to remove an alkali component contained in the active carbon, followed by washing with water and drying. The activation method of the active carbon may be either a gas activation method or a chemical activation method.

From the viewpoint of catalytic activity, the carbon content in the active carbon is preferably from 95 to 99.95 by mass, and more preferably from 97 to 99.9% by mass.

The shape of the active carbon is not particularly limited, and it may be a shape of powder, granule, fiber, pellet, honeycomb, or the like.

From the viewpoint of enhancing the catalytic activity, a specific surface area of the active carbon is preferably from 500 to 4,000 m$^2$/g, more preferably from 1,000 to 3,500 m$^2$/g, and still more preferably from 1,500 to 3,000 m$^2$/g.

The above-described specific surface area of the active carbon is measured by the mercury press-in method using a dry catalyst powder.

(Preparation of Palladium Catalyst (A) Supported on Active Carbon)

Examples of a method of supporting palladium on active carbon include an impregnation method, an ion exchange method, a CVD method, and the like, an impregnation method and an ion exchange method are preferable, and an impregnation method is more preferable.

In order to support palladium on active carbon, it is preferable to use a palladium salt.

Examples of the palladium salt include Pd(OH)$_2$, PdCl$_2$, Pd(OAc)$_2$, Pd(NH$_4$)Cl$_2$, [Pd(NH$_3$)$_4$]Cl$_2$, and the like. Of these, palladium hydroxide: Pd(OH)$_2$, palladium chloride: PdCl$_2$, and palladium acetate: Pd(OAc)$_2$ are preferable, and palladium hydroxide and palladium chloride are more preferable. Examples of the impregnation method using a palladium salt include a method of dissolving a palladium salt in an appropriate solvent and dispersing and contacting peat-derived active carbon, or the like.

The supporting amount of palladium on the active carbon is preferably from 0.1 to 15% by mass, more preferably from 0.5 to 10% by mass, and still more preferably from 1 to 8% by mass in the palladium catalyst (A). When the supporting amount of palladium is less than 0.1% by mass, the catalytic activity becomes easily insufficient, whereas when it is more than 15% by mass, the possibility of giving an adverse influence such as sintering, etc. becomes high on the occasion of supporting.

After supporting palladium on the active carbon, it is preferable to carry out calcination at from 200 to 700° C., and it is more preferable to carry out calcination at from 300 to 600° C.

The pH of the palladium catalyst (A) is preferably from 7.0 to 12.0, and from the viewpoint of rendering the fragrance notes of the obtained 1-(2-t-butylcyclohexyloxy)-2-alkanol favorable, the pH of the palladium catalyst (A) is preferably from 7.0 to 10.0, and more preferably from 7.0 to 9.0. In addition, from the viewpoint of enhancing the yield of the 1-(2-t-butylcyclohexyloxy)-2-alkanol, the pH of the palladium catalyst (A) is preferably from 7.5 to 9.5, more preferably from 7.5 to 9.0, still more preferably from 7.8 to 9.0, yet still more preferably from 7.9 to 8.9, and even yet still more preferably from 8.0 to 8.8.

By allowing the pH of the palladium catalyst (A) to fall within the foregoing range, the adsorption of the raw material onto the catalyst is accelerated without causing decomposition of the obtained 1-(2-t-butylcyclohexyloxy)-2-alkanol, and therefore, it may be considered that the yield of the 1-(2-t-butylcyclohexyloxy)-2-alkanol is enhanced.

Incidentally, the pH of the palladium catalyst (A) refers to a pH of a mixture obtained by mixing the palladium catalyst (A) with pure water in an amount of 10 times by mass.

<Metal Catalyst (B)>

In the present invention, the metal catalyst (B) containing one or more kinds of members selected from ruthenium, rhodium, platinum, and nickel is used in addition to the above-described palladium catalyst (A).

Among the above-described metal components which are used for the metal catalyst (B), from the viewpoint of enhancing the yield and the trans-isomer content, ruthenium, rhodium, and platinum are preferable, ruthenium and rhodium are more preferable, and ruthenium is still more preferable.

The metal catalyst (B) is preferably a supported catalyst supported on a carrier. The carrier is preferably an inorganic carrier. Examples of the inorganic carrier include one or more kinds of carriers selected from active carbon, alumina, silica, silica magnesia, and zeolite. Of these, active carbon is more preferable from the viewpoint of catalytic activity.

Examples of the active carbon include the same active carbons as those described above, and the active carbon can be prepared in the same manner as that described above.

From the viewpoint of preventing sintering while increasing the catalytic activity, the supporting amount of the metal component is preferably from 0.05 to 20% by mass, more preferably from 0.1 to 15% by mass, and still more preferably from 0.5 to 10% by mass of the whole of the metal catalyst (B).

In the case where the metal catalyst (B) is a supported catalyst, the metal catalyst (B) refers to the whole including the metal and the carrier.

(Preparation of Metal Catalyst (B))

The preparation of the metal catalyst (B) can be carried out by a known method. For example, when the case of using ruthenium as the metal component is taken as an example, first of all, the above-described inorganic carrier is added to and suspended in a medium such as ion-exchanged water, etc.; a solution having a ruthenium compound (e.g., a chloride, nitrate, formate, or ammonium salt of ruthenium, or the like) dissolved in an aqueous solvent such as ion-exchanged water, etc. is added to this suspension; and the resultant is adjusted to a temperature of from about 20 to 95° C. while stirring, upon heating as the need arises. Subsequently, an alkali (e.g., ammonia water, a carbonate or hydroxide of an alkali metal such as sodium, potassium, etc., or the like) is added to the resulting suspension to adjust the pH to from about 4 to 12, thereby achieving hydrolysis, followed by aging to support the ruthenium component on the inorganic carrier.

Subsequently, for example, a reducing agent such as formaldehyde, hydrazine, sodium borohydride, etc. is added; the resultant is subjected to a reducing treatment at a temperature of from about 20 to 95° C., upon heating as the need arises; thereafter, solid-liquid separation is carried out; and the resulting solid is washed with water and dried, whereby the metal catalyst (B) can be obtained.

The pH of the metal catalyst (B) is preferably from 6.0 to 12.0, and from the viewpoint of enhancing the yield of the 1-(2-t-butylcyclohexyloxy)-2-alkanol, the pH of the metal catalyst (B) is preferably from 7.0 to 9.0, and more preferably from 7.5 to 8.0. Incidentally, the pH of the metal catalyst (B) refers to a pH of a mixture obtained by mixing the metal catalyst (B) with pure water in an amount of 10 times by mass.

(Palladium Catalyst (A) and Metal Catalyst (B))

From the viewpoint of catalytic activity, a mass ratio of the palladium catalyst (A) and the metal catalyst (B), [(A)/(B)], is preferably from 1,000/1 to 1/1, and more preferably from 100/1 to 5/1.

In addition, from the viewpoint of enhancing the trans-isomer content, a mass ratio of palladium in the palladium catalyst (A) and the metal in the metal catalyst (B), [{palladium in the catalyst (A)}/{metal in the catalyst (B)}], is preferably from 80/20 to 99/1, more preferably from 85/15 to 95/5, and still more preferably from 90/10 to 95/5.

A mixing method of the palladium catalyst (A) and the metal catalyst (B) is not particularly limited. Examples thereof include (i) a method of separately adding the catalysts (A) and (B) at the time of the reaction; (ii) a method of preparing a mixed catalyst such as a coprecipitation catalyst, etc. prior to the reaction; and the like. From the viewpoint of adjusting the mass ratio of the palladium catalyst (A) and the metal catalyst (B), the method (i) of separately adding the catalysts (A) and (B) at the time of the reaction is preferable.

A total use amount of the palladium catalyst (A) and the metal catalyst (B) is preferably from 0.01 to 10% by mass, and more preferably from 0.05 to 5% by mass relative to 1-(2-t-butylphenyloxy)-2-alkanol as the raw material.

<Basic Substance>

From the viewpoint of obtaining the 1-(2-t-butylcyclohexyloxy)-2-alkanol having a high trans-isomer content and a strong woody or amber-like fragrance and also having very excellent persistence of aroma, it is preferable to add a basic substance in the raw material mixture containing the 1-(2-t-butylphenyloxy)-2-alkanol represented by the formula (1) in the hydrogenation step in the production method of the present invention.

The basic substance is preferably one or more kinds of members selected from an amine, an alkali metal compound, and an alkaline earth metal compound; from the viewpoint of increasing the trans-isomer content, an amine and an alkali metal compound are preferable; and from the viewpoint of increasing the solubility in the raw material, an amine is more preferable.

The addition amount of the basic substance is preferably from 1 to 3,000 ppm in terms of a nitrogen atom content or a metal content relative to 1-(2-t-butylphenyloxy)-2-alkanol represented by the formula (1) as the raw material.

(Amine)

Examples of the amine include ammonia, a monovalent primary amine, a monovalent secondary amine, a monovalent tertiary amine, and a polyvalent amine. Of these, from the viewpoints of efficiently increasing the pH of the raw material mixture by means of addition of a small amount and increasing the yield of the 1-(2-t-butylcyclohexyloxy)-2-alkanol and the trans-isomer content, a monovalent primary amine, a monovalent secondary amine, and a polyvalent amine are preferable, a monovalent primary amine and a polyvalent amine are more preferable, and a polyvalent amine is still more preferable. From the viewpoint of solubility in the raw material, the carbon number of the amine is preferably from 0 to 30, and more preferably from 2 to 18.

Specific examples of the monovalent primary amine include methylamine, ethylamine, n-propylamine, isopropylamine, n-butylamine, isobutylamine, sec-butylamine, tert-butylamine, 3-methoxypropylamine, amylamine, hexylamine, cyclohexylamine, aniline, octylamine, decylamine, and the like. Of these, from the viewpoint of increasing the solubility in the raw material, a chain or cyclic monovalent primary amine having from 4 to 14 carbon atoms, and especially from 6 to 12 carbon atoms, such as hexylamine, cyclohexylamine, aniline, octylamine, decylamine, etc., is preferable, and above all, octylamine is preferable.

Specific examples of the monovalent secondary amine include dimethylamine, diethylamine, dipropylamine, diisopropylamine, dibutylamine, diisobutylamine, N-methylbutylamine, N-ethylbutylamine, N-t-butylisopropylamine, bis(2-methoxyethyl)amine, N-methylcyclohexylamine, dicyclohexylamine, N-methylaniline, pyrrolidine, piperidine, 2-methylpiperidine, 2,2,6,6-tetramethylpiperidine, morpholine, perhydroindole, 1-aza-12-crown-4, and the like. Of these, from the viewpoint of increasing the solubility in the raw material, a chain or cyclic monovalent secondary amine having from 2 to 14 carbon atoms, and especially from 4 to 10 carbon atoms, such as dipropylamine, diisopropylamine, dibutylamine, diisobutylamine, N-ethylbutylamine, N-t-butylisopropylamine, morpholine, etc., is preferable. Above all, diisopropylamine and morpholine that are a chain or cyclic monovalent secondary amine having from 4 to 8 carbon atoms are preferable, and diisopropylamine is more preferable.

Specific examples of the monovalent tertiary amine include trimethylamine, triethylamine, tripropylamine, N,N-diisopropylethylamine, triisobutylamine, tridodecylamine, N,N-diethylcyclohexylamine, pyridine, N,N-dimethylaniline, N-methylpyrrolidine, N-ethylpiperidine, quinoline, and the like.

Specific examples of the polyvalent amine include ethylenediamine, 1,2-diaminopropane, 1,4-diaminobutane, N-methylethylenediamine, N-isopropylethylenediamine, N,N'-dimethylethylenediamine, N,N-dimethylethylenediamine, N,N-diethyl-N'-methylethylenediamine, N,N,N',N'-tetramethyl-1,4-butanediamine, tris(2-aminoethyl)amine, piperazine, 1-methyl-4-(methylamino)-piperidine, 1-methylpiperazine, 1,4-dimethylpiperazine, 1,4,7-triazacyclononane, 1,4-diazabicyclo(2.2.2)octane, and the like. Of these, from the viewpoint of increasing the solubility in the raw material, a chain or cyclic polyvalent amine having from 2 to 6 carbon atoms, and especially from 2 to 4 carbon atoms, such as ethylenediamine, N,N'-dimethylethylenediamine, piperazine, 1,4-dimethylpiperazine, etc., is preferable, and above all, piperazine is preferable.

The addition amount of the amine is preferably from 1 to 3,000 ppm in terms of a nitrogen atom content relative to 1-(2-t-butylphenyloxy)-2-alkanol as the raw material; from the viewpoints of more efficiently adjusting the pH to an appropriate range, increasing the yield, and enhancing the trans-isomer content, the addition amount of the amine is more preferably from 100 to 3,000 ppm, and still more preferably from 200 to 1,500 ppm; and in particular, from the viewpoint of enhancing the trans-isomer content, the addition amount of the amine is preferably from 400 to 1,200 ppm, and more preferably from 400 to 800 ppm.

(Alkali Metal Compound)

Examples of the alkali metal compound include a hydroxide, an alcoholate, a carboxylate, a carbonate, a hydrogencarbonate, etc. of an alkali metal, and from the viewpoint of solubility, a hydroxide and a carbonate are preferable, and a carbonate is more preferable.

Examples of the hydroxide include sodium hydroxide, lithium hydroxide, potassium hydroxide, cesium hydroxide, and the like. Of these, sodium hydroxide and potassium hydroxide are preferable, and sodium hydroxide is more preferable.

Examples of the alcoholate include sodium methylate, potassium ethylate, and the like, and examples of the carboxylate include sodium acetate, potassium acetate, and the like.

Examples of the carbonate and the hydrogencarbonate include sodium carbonate, sodium hydrogencarbonate, lithium carbonate, potassium carbonate, and the like. Of these, sodium carbonate and potassium carbonate are preferable, and potassium carbonate is more preferable.

(Alkaline Earth Metal Compound)

Examples of the alkaline earth metal compound include a hydroxide, a carbonate, a hydrogencarbonate, etc. of an alkaline earth metal.

Examples of the hydroxide include calcium hydroxide, barium hydroxide, and the like, and examples of the carbonate include calcium carbonate and the like.

The addition amount of the alkali metal compound or the alkaline earth metal compound is preferably from 1 to 3,000 ppm in terms of a metal content relative to 1-(2-t-butylphenyloxy)-2-alkanol as the raw material, and from the viewpoints of more efficiently adjusting the pH to an appropriate range, increasing the yield, and enhancing the trans-isomer content, the addition amount of the alkali metal compound or the alkaline earth metal compound is more preferably from 1 to 1,000 ppm, still more preferably from 10 to 500 ppm, and yet still more preferably from 30 to 200 ppm.

The alkali metal compound or the alkaline earth metal compound can also be used upon being contained in the palladium catalyst (A) and/or the metal catalyst (B), and it is preferable to obtain the palladium catalyst (A) and/or the metal catalyst (B) having an alkali metal compound or an alkaline earth metal compound impregnated therein by impregnating an aqueous solution of the metal compound. From the viewpoint of operability, it is more preferable to use the palladium catalyst (A).

The above-described basic substance can be used solely or in combination of two or more kinds thereof.

<Hydrogenation Step>

In the hydrogenation step in the present invention, the hydrogenation reaction is, for example, carried out by adding the 1-(2-t-butylphenyloxy)-2-alkanol, the palladium catalyst (A), and the metal catalyst (B) containing one or more kinds of members selected from ruthenium, rhodium, platinum, and nickel, and preferably a basic compound, and an arbitrary organic solvent as the need arises in a pressure-resistant reactor such as an autoclave, etc. and further introducing hydrogen into the reactor.

Examples of the organic solvent which is used for the hydrogenation reaction include one or more kinds of members selected from an alcohol and a hydrocarbon. Examples of the alcohol include methanol, ethanol, isopropanol, and the like, and examples of the hydrocarbon include hexane, cyclohexane, etc. Of these, an alcohol is preferable, and isopropanol is more preferable.

From the viewpoint of productivity, the amount of the organic solvent is preferably not more than 500% by mass, more preferably not more than 10% by mass, still more preferably not more than 5% by mass, yet still more preferably not more than 1% by mass, even still more preferably substantially 0% by mass, and even yet still more preferably 0% by mass relative to the 1-(2-t-butylphenyloxy)-2-alkanol. It is even still more preferable that the organic solvent is not contained within the reactor in the hydrogenation step. That is, when the hydrogenation reaction is carried out in the absence of a solvent, a collision rate between the substrate and the catalyst increases, the reaction is easy to proceed, and the residual amount of an intermediate decreases, and hence, such is preferable.

Here, the pH of the raw material mixture containing the 1-(2-t-butylphenyloxy)-2-alkanol represented by the formula (1) is adjusted to from 7.5 to 10.0. Here, the pH of the raw material mixture means a pH of an aqueous layer on the occasion of mixing the whole of the mixture in the pressure-resistant reactor immediately before commencement of the reaction with pure water in an amount of 30% by mass relative to the mixture.

From the viewpoint of obtaining the 1-(2-t-butylcyclohexyloxy)-2-alkanol having a high trans-isomer content and a strong woody or amber-like fragrance and also having very excellent persistence of aroma, the pH of the raw material mixture is from 7.5 to 10.0, preferably from 8.5 to 10.0, more preferably from 9.0 to 10.0, still more preferably from 9.5 to 10.0, and yet still more preferably from 9.7 to 10.0.

From the viewpoint of obtaining the 1-(2-t-butylcyclohexyloxy)-2-alkanol in a high yield, the pH of the raw material mixture is from 7.5 to 10.0, preferably from 7.5 to 9.0, more preferably from 7.5 to 8.5, and still more preferably from 7.9 to 8.5.

The adjustment of the pH can be carried out by a method of using a material having a higher pH for the palladium catalyst (A) or the metal catalyst (B), or a method of adding a basic substance. As for the adjustment of the pH, from the viewpoint of obtaining the 1-(2-t-butylcyclohexyloxy)-2-alkanol having a high trans-isomer content and a strong woody or amber-like fragrance and also having very excellent persistence of aroma, a method of adding a basic substance is preferable, and from the viewpoint of obtaining the 1-(2-t-butylcyclohexyloxy)-2-alkanol in a high yield, a method of using a material having a higher pH for the palladium catalyst (A) or the metal catalyst (B) is preferable.

A hydrogen pressure in the hydrogenation step is preferably from 0.1 to 15 MPa, more preferably from 0.5 to 10 MPa, and still more preferably from 1 to 5 MPa. Here, the "hydrogen pressure" refers to a partial pressure of hydrogen in the pressure-resistant reactor at the time of the hydrogenation reaction.

From the viewpoint of increasing the content of the trans-isomer occupying in the product, a reaction temperature in the hydrogenation step is preferably from 50 to 300° C., more preferably from 100 to 250° C., and still more preferably from 130 to 200° C. A reaction time is preferably from 1 to 30 hours, more preferably from 2 to 20 hours, and still more preferably from 3 to 10 hours.

The product obtained in the hydrogenation step can be purified by means of filtration, distillation, column chromatography, or the like, as the need arises.

According to the production method of the present invention, the 1-(2-t-butylcyclohexyloxy)-2-alkanol having the trans-isomer content of 41% by mass or more can be efficiently produced, and so long as a suitable condition is adopted, the product having the trans-isomer content of from 43 to 52% by mass can be efficiently produced.

[Perfume Composition]

The perfume composition of the present invention is one containing the 1-(2-t-butylcyclohexyloxy)-2-alkanol obtained by the above-described production method of the present invention.

From the viewpoints of fragrance and fragrance notes, the content of the 1-(2-t-butylcyclohexyloxy)-2-alkanol in the perfume composition of the present invention is preferably from 0.01 to 99% by mass, more preferably from 0.1 to 15% by mass, and still more preferably from 1 to 10% by mass.

In addition, the perfume composition of the present invention can contain generally used other perfume component or a formulated perfume having a desired composition.

Examples of other perfume component which can be used include an alcohol other than the 1-(2-t-butylcyclohexyloxy)-2-alkanol, a hydrocarbon, a phenol, an ester, a carbonate, an aldehyde, a ketone, an acetal, an ether, a carboxylic acid, a lactone, a nitrile, a Schiff base, a natural essential oil, a natural extract, and the like. Of these, an alcohol, an ester, and a lactone are preferable, and an alcohol and an ester are more preferable. These perfume components can be used solely or in combination of two or more kinds thereof.

As for the above-described embodiment, the present invention discloses the following methods of producing a 1-(2-t-butylcyclohexyloxy)-2-alkanol and perfume compositions.

<1> A method of producing a 1-(2-t-butylcyclohexyloxy)-2-alkanol including a step of adjusting a raw material mixture containing a 1-(2-t-butylphenyloxy)-2-alkanol represented by the formula (1) to a pH of from 7.5 to 10.0 and hydrogenating it in the presence of a palladium catalyst (A) and a metal catalyst (B) containing one or more kinds of members selected from ruthenium, rhodium, platinum, and nickel.

[Chem. 4]

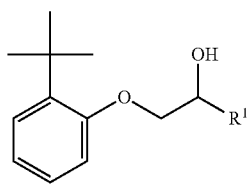

(1)

(In the formula, $R^1$ is a methyl group or an ethyl group.)

<2> The method of producing a 1-(2-t-butylcyclohexyloxy)-2-alkanol as set forth above in <1>, wherein in the hydrogenation step, a basic substance is preferably added in the raw material mixture.

<3> The method of producing a 1-(2-t-butylcyclohexyloxy)-2-alkanol as set forth above in <2>, wherein the basic substance is preferably one or more kinds of members selected from an amine, an alkali metal compound, and an alkaline earth metal compound, more preferably one or more kinds of members selected from an amine and an alkali metal compound, and still more preferably an amine.

<4> The method of producing a 1-(2-t-butylcyclohexyloxy)-2-alkanol as set forth above in <2> or <3>, wherein the addition amount of the basic substance is preferably from 1 to 3,000 ppm in terms of a nitrogen atom content or a metal content relative to the 1-(2-t-butylphenyloxy)-2-alkanol represented by the formula (1).

<5> The method of producing a 1-(2-t-butylcyclohexyloxy)-2-alkanol as set forth above in <3>, wherein the amine is preferably one or more kinds of members selected from ammonia, a monovalent primary amine, a monovalent secondary amine, a monovalent tertiary amine, and a polyvalent amine, more preferably one or more kinds of members selected from a monovalent primary amine, a monovalent secondary amine, and a polyvalent amine, still more preferably one or more kinds of members selected from a monovalent primary amine and a polyvalent amine, and yet still more preferably a polyvalent amine.

<6> The method of producing a 1-(2-t-butylcyclohexyloxy)-2-alkanol as set forth above in <3> or <5>, wherein the addition amount of the amine is preferably 1 ppm or more and not more than 3,000 ppm, more preferably 100 ppm or more, still more preferably 200 ppm or more, and yet still more preferably 400 ppm or more, and more preferably not more than 1,500 ppm, still more preferably not more than 1,200 ppm, and yet still more preferably not more than 800 ppm in terms of a nitrogen atom content relative to the 1-(2-t-butylphenyloxy)-2-alkanol represented by the formula (1).

<7> The method of producing a 1-(2-t-butylcyclohexyloxy)-2-alkanol as set forth above in <3>, wherein the addition amount of the alkali metal compound or the alkaline earth metal compound is preferably 1 ppm or more and not more than 1,000 ppm, more preferably 10 ppm or more, and still more preferably 30 ppm or more, and more preferably not more than 500 ppm, and still more preferably not more than 200 ppm in terms of a metal content relative to the 1-(2-t-butylphenyloxy)-2-alkanol represented by the formula (1).

<8> The method of producing a 1-(2-t-butylcyclohexyloxy)-2-alkanol as set forth above in any one of <1> to <7>, wherein a mass ratio of palladium in the palladium catalyst (A) and one or more kinds of metals selected from ruthenium, rhodium, platinum, and nickel in the metal catalyst (B), [(A)/(B)], is preferably from 80/20 to 99/1, more preferably from 85/15 to 95/5, and still more preferably from 90/10 to 95/5.

<9> The method of producing a 1-(2-t-butylcyclohexyloxy)-2-alkanol as set forth above in any one of <1> to <8>, wherein the amount of an organic solvent in the hydrogenation step is preferably not more than 10% by mass, more preferably not more than 5% by mass, still more preferably not more than 1% by mass, and yet still more preferably substantially 0% by mass relative to the 1-(2-t-butylphenyloxy)-2-alkanol.

<10> The method of producing a 1-(2-t-butylcyclohexyloxy)-2-alkanol as set forth above in <9>, wherein the amount of the organic solvent in the hydrogenation step is preferably 0% by mass relative to the 1-(2-t-butylphenyloxy)-2-alkanol, and more preferably, the organic solvent is not contained within a reactor in the hydrogenation step.

<11> The method of producing a 1-(2-t-butylcyclohexyloxy)-2-alkanol as set forth above in any one of <1> to <10>, wherein the content of a trans-isomer of the 1-(2-t-butylcyclohexyloxy)-2-alkanol is preferably 41% by mass or more, and more preferably 43% by mass or more, and preferably not more than 52% by mass.

<12> The method of producing a 1-(2-t-butylcyclohexyloxy)-2-alkanol as set forth above in any one of <1> to <11>, wherein $R^1$ in the formula (1) is preferably an ethyl group.

<13> The method of producing a 1-(2-t-butylcyclohexyloxy)-2-alkanol as set forth above in any one of <1> to <12>, wherein the palladium catalyst (A) is preferably a supported catalyst supported on a carrier.

<14> The method of producing a 1-(2-t-butylcyclohexyloxy)-2-alkanol as set forth above in <13>, wherein the carrier of the palladium catalyst (A) is preferably an inorganic carrier, and more preferably one or more kinds of carriers selected from active carbon, alumina, silica, silica magnesia, and zeolite.

<15> The method of producing a 1-(2-t-butylcyclohexyloxy)-2-alkanol as set forth above in <14>, wherein the inorganic carrier is active carbon, and more preferably one or more kinds of active carbons selected from those derived from peat, bituminous coal, anthracite coal, lignite, wood, and coconut shell.

<16> The method of producing a 1-(2-t-butylcyclohexyloxy)-2-alkanol as set forth above in <15>, wherein the active carbon is preferably peat-derived active carbon.

<17> The method of producing a 1-(2-t-butylcyclohexyloxy)-2-alkanol as set forth above in <15> or <16>, wherein the carbon content in the active carbon is preferably 95% by mass or more and not more than 99.95% by mass, and more preferably 97% by mass or more and not more than 99.9% by mass.

<18> The method of producing a 1-(2-t-butylcyclohexyloxy)-2-alkanol as set forth above in any one of <15> to <17>, wherein a specific surface area of the active carbon is preferably 500 m$^2$/g or more and not more than 4,000 m$^2$/g, more preferably 1,000 m$^2$/g or more, and still more preferably 1,500 m$^2$/g or more, and more preferably not more than 3,500 m$^2$/g, and still more preferably not more than 3,000 m$^2$/g.

<19> The method of producing a 1-(2-t-butylcyclohexyloxy)-2-alkanol as set forth above in any one of <15> to <18>, wherein the supporting amount of palladium in the palladium catalyst (A) supported on the active carbon is preferably 0.1% by mass or more and not more than by mass, more preferably 0.5% by mass or more, and still more preferably 1% by mass or more, and more preferably not more than 10% by mass, and still more preferably not more than 8% by mass.

<20> The method of producing a 1-(2-t-butylcyclohexyloxy)-2-alkanol as set forth above in any one of <15> to <19>, wherein the palladium catalyst (A) supported on the active carbon is preferably one obtained by an impregnation method using a palladium salt.

<21> The method of producing a 1-(2-t-butylcyclohexyloxy)-2-alkanol as set forth above in <20>, wherein the palladium salt is preferably one or more members selected from Pd(OH)$_2$, PdCl$_2$, Pd(OAc)$_2$, Pd(NH$_4$)Cl$_2$, and [Pd(NH$_3$)$_4$]Cl$_2$, more preferably one or more members selected from Pd(OH)$_2$, PdCl$_2$, and Pd(OAc)$_2$, and still more preferably one or more members selected from Pd(OH)$_2$ and PdCl$_2$.

<22> The method of producing a 1-(2-t-butylcyclohexyloxy)-2-alkanol as set forth above in any one of <15> to <21>, wherein the palladium catalyst (A) supported on the active carbon is obtained by supporting palladium on active carbon and then carrying out calcination at preferably 200° C. or higher and not higher than 700° C., and more preferably 300° C. or higher and not higher than 600° C.

<23> The method of producing a 1-(2-t-butylcyclohexyloxy)-2-alkanol as set forth above in any one of <1> to <22>, wherein the pH of the palladium catalyst (A) is preferably 7.0 or more and not more than 12.0, more preferably 7.0 or more, still more preferably 7.5 or more, yet still more preferably 7.8 or more, even still more preferably 7.9 or more, and even yet still more preferably 8.0 or more, and more preferably not more than 10.0, still more preferably not more than 9.5, yet still more preferably not more than 9.0, even still more preferably not more than 9.0, even yet still more preferably not more than 8.9, and yet even still more preferably not more than 8.8.

<24> The method of producing a 1-(2-t-butylcyclohexyloxy)-2-alkanol as set forth above in any one of <1> to <23>, wherein the metal catalyst (B) is preferably a supported catalyst supported on a carrier.

<25> The method of producing a 1-(2-t-butylcyclohexyloxy)-2-alkanol as set forth above in <24>, wherein the metal component of the metal catalyst (B) is preferably one or more kinds of members selected from ruthenium, rhodium, and platinum, more preferably one or more kinds of members selected from ruthenium and rhodium, and still more preferably ruthenium.

<26> The method of producing a 1-(2-t-butylcyclohexyloxy)-2-alkanol as set forth above in <24> or <25>, wherein the carrier of the metal catalyst (B) is preferably an inorganic carrier, more preferably one or more kinds of carriers selected from active carbon, alumina, silica, silica magnesia, and zeolite, and still more preferably active carbon.

<27> The method of producing a 1-(2-t-butylcyclohexyloxy)-2-alkanol as set forth above in any one of <24> to <26>, wherein the supporting amount of the metal component of the metal catalyst (B) is preferably 0.05% by mass or more and not more than 20% by mass, more preferably 0.1% by mass or more, and still more preferably 0.5% by mass or more, and more preferably not more than 15% by mass, and still more preferably not more than 10% by mass of the whole of the metal catalyst (B).

<28> The method of producing a 1-(2-t-butylcyclohexyloxy)-2-alkanol as set forth above in any one of <1> to <27>, wherein the pH of the metal catalyst (B) is preferably 6.0 or more and not more than 12.0, more preferably 7.0 or more, and still more preferably 7.5 or more, and more preferably not more than 9.0, and still more preferably not more than 8.0.

<29> The method of producing a 1-(2-t-butylcyclohexyloxy)-2-alkanol as set forth above in any one of <1> to <28>, wherein a total use amount of the palladium catalyst (A) and the metal catalyst (B) is preferably 0.01% mass or more and not more than 10% by mass, and more preferably 0.05% mass or more and not more than 5% mass relative to the 1-(2-t-butylphenyloxy)-2-alkanol represented by the formula (1).

<30> The method of producing a 1-(2-t-butylcyclohexyloxy)-2-alkanol as set forth above in any one of <1> to <29>, wherein the organic solvent which is used for the hydrogenation reaction is preferably one or more kinds of members selected from an alcohol and a hydrocarbon, more preferably one or more kinds of members selected from methanol, ethanol, and isopropanol, and still more preferably isopropanol.

<31> The method of producing a 1-(2-t-butylcyclohexyloxy)-2-alkanol as set forth above in any one of <1> to <30>, wherein the pH of the raw material mixture is preferably 8.5 or more and not more than 10.0, more preferably 9.0 or more, still more preferably 9.5 or more, and yet still more preferably 9.7 or more.

<32> The method of producing a 1-(2-t-butylcyclohexyloxy)-2-alkanol as set forth above in any one of <1> to <30>, wherein the pH of the raw material mixture is preferably 7.5 or more and not more than 9.0, and more preferably 7.9 or more, and more preferably not more than 9.0, and still more preferably not more than 8.5.

<33> The method of producing a 1-(2-t-butylcyclohexyloxy)-2-alkanol as set forth above in any one of <1> to <32>, wherein a hydrogen pressure in the hydrogenation step is preferably 0.1 MPa or more and not more than 15 MPa, more preferably 0.5 MPa or more, and still more preferably 1 MPa or more, and more preferably not more than 10 MPa, and still more preferably not more than 5 MPa.

<34> The method of producing a 1-(2-t-butylcyclohexyloxy)-2-alkanol as set forth above in any one of <1> to <33>, wherein a reaction temperature in the hydrogenation step is preferably 50° C. or higher and not higher than 300° C., more preferably 100° C. or higher, and still more preferably 130° C. or higher, and more preferably not higher than 250° C., and still more preferably not higher than 200° C.

<35> A perfume composition containing the 1-(2-t-butylcyclohexyloxy)-2-alkanol obtained by the production method as set forth above in any one of <1> to <34>.

<36> The perfume composition as set forth above in <35>, wherein the content of the 1-(2-t-butylcyclohexyloxy)-2-alkanol in the perfume composition is preferably 0.01% by mass or more and not more than 99% by mass, more preferably 0.1% by mass or more, and still more preferably 1% by mass or more, and more preferably not more than 15% by mass, and still more preferably not more than 10% by mass.

<37> The perfume composition as set forth above in <35> or <36>, wherein the perfume composition preferably contains one or more members selected from an alcohol other than the 1-(2-t-butylcyclohexyloxy)-2-alkanol, a hydrocarbon, a phenol, an ester, a carbonate, an aldehyde, a ketone, an acetal, an ether, a carboxylic acid, a lactone, a nitrile, a Schiff base, a natural essential oil, and a natural extract.

<38> Use of the 1-(2-t-butylcyclohexyloxy)-2-alkanol obtained by the production method as set forth above in any one of <1> to <34> as a perfume.

EXAMPLES

In the following Examples and Comparative Examples, to term "%" is "% by mass" unless otherwise indicated.

Example 1

Production of 1-(2-t-butylcyclohexyloxy)-2-butanol

In a 500-mL autoclave, 150 g (675 mmoles) of 1-(2-t-butylphenyloxy)-2-butanol, 2.85 g of a 2% active carbon-supported palladium catalyst (palladium: 0.057 g) (manufactured by N.E. Chemcat Corporation, pH: 7.3), 0.15 g of a 5% active carbon-supported ruthenium catalyst (ruthenium: 0.0057 g) (manufactured by N.E. Chemcat Corporation, pH: 7.2), and 1.5 g of n-octylamine (11.6 mmoles; this is corresponding to 1,100 ppm in terms of a nitrogen atom content relative to 1-(2-t-butylphenyloxy)-2-butanol) as the raw material were added and allowed to react at a hydrogen pressure of 2.0 MPa and 190° C. for 7 hours. The pH of the raw material mixture at the time of commencement of the reaction was 9.2.

After termination of the reaction, the catalysts were filtered, and distillation was carried out to obtain 1-(2-t-butylcyclohexyloxy)-2-butanol in a yield of 78%. An isomer ratio of 1-(2-t-butylcyclohexyloxy)-2-butanol as the product was analyzed by means of gas chromatography. As a result, a ratio of cis-isomer/trans-isomer was found to be 54/46 (mass ratio). The analysis was carried out in the same manner in the following Examples and Comparative Examples. Results are shown in Tables 1 and 2.

Example 2

Production of 1-(2-t-butylcyclohexyloxy)-2-butanol 1-(2-t-butylcyclohexyloxy)-2-butanol was obtained by carrying out the reaction in the same manner as that in Example 1, except that in Example 1, the 2% active carbon-supported palladium catalyst (manufactured by N.E. Chemcat Corporation, pH: 7.3) was changed to a 2% active carbon-supported palladium catalyst (manufactured by N.E. Chemcat Corporation, pH: 7.9); and that the pH of the raw material mixture at the time of commencement of the reaction was changed to 9.9. Results are shown in Table 1.

Comparative Example 1

Production of 1-(2-t-butylcyclohexyloxy)-2-butanol 1-(2-t-butylcyclohexyloxy)-2-butanol was obtained by carrying out the reaction in the same manner as that in Example 1, except that in Example 1, the n-octylamine was not added; and the pH of the raw material mixture at the time of commencement of the reaction was changed to 6.8. Results are shown in Table 1.

Example 3

Production of 1-(2-t-butylcyclohexyloxy)-2-butanol

In a 500-ml, autoclave, 50 g (238 mmoles) of 1-(2-t-butylphenyloxy)-2-butanol, 150 g of isopropanol, 0.95 g of a 2% active carbon-supported palladium catalyst (palladium: 0.019 g) (manufactured by N.E. Chemcat Corporation, supporting amount of palladium: 2%, pH: 7.3), 0.05 g of a 5% active carbon-supported ruthenium catalyst (ruthenium: 0.0025 g) (manufactured by N.E. Chemcat Corporation, pH: 7.2), and 0.1 g of morpholine (1.15 mmoles; this is corresponding to 322 ppm in terms of a nitrogen atom content relative to 1-(2-t-butylphenyloxy)-2-butanol) as the raw material were added and allowed to react at a hydrogen pressure of 2.0 MPa and 190° C. for 7 hours. The pH of the raw material mixture at the time of commencement of the reaction was 7.5.

After termination of the reaction, the catalysts were filtered, and distillation was carried out to obtain 1-(2-t-butylcyclohexyloxy)-2-butanol. Results are shown in Table 1.

Comparative Example 2

Production of 1-(2-t-butylcyclohexyloxy)-2-butanol 1-(2-t-butylcyclohexyloxy)-2-butanol was obtained by carrying out the reaction in the same manner as that in Example 3, except that in Example 3, the morpholine was not added; and the pH of the raw material mixture at the time of commencement of the reaction was changed to 7.3. Results are shown in Table 1.

Example 4

Production of 1-(2-t-butylcyclohexyloxy)-2-butanol 1-(2-t-butylcyclohexyloxy)-2-butanol was obtained by carrying out the reaction in the same manner as that in Example 3, except that in Example 3, the morpholine was not added; the 2% active carbon-supported palladium catalyst (manufactured by N.E. Chemcat Corporation, pH: 7.3) was changed to a 2% active carbon-supported palladium catalyst (manufactured by N.E. Chemcat Corporation, pH: 7.6); and the pH of the raw material mixture at the time of commencement of the reaction was changed to 7.5. Results are shown in Table 1.

Example 5

Production of 1-(2-t-butylcyclohexyloxy)-2-butanol 1-(2-t-butylcyclohexyloxy)-2-butanol was obtained by carrying out the reaction in the same manner as that in Example 4, except that in Example 4, the 2% active carbon-supported palladium catalyst (manufactured by N.E. Chemcat Corporation, pH: 7.6) was changed to a 2% active carbon-supported palladium catalyst (manufactured by N.E. Chemcat Corporation, pH: 8.5); and the pH of the raw material mixture at the time of commencement of the reaction was changed to 8.3. Results are shown in Table 1.

Example 6

Production of 1-(2-t-butylcyclohexyloxy)-2-butanol 1-(2-t-butylcyclohexyloxy)-2-butanol was obtained by carrying out the reaction in the same manner as that in Example 4, except that in Example 4, the 2% active carbon-supported palladium catalyst (manufactured by N.E. Chemcat Corporation, pH: 7.6) was changed to a 2% active carbon-supported palladium catalyst (manufactured by N.E. Chemcat Corporation, pH: 9.2); and the pH of the raw material mixture at the time of commencement of the reaction was changed to 8.9. Results are shown in Table 1.

Example 7

Production of 1-(2-t-butylcyclohexyloxy)-2-butanol 1-(2-t-butylcyclohexyloxy)-2-butanol was obtained by carrying out the reaction in the same manner as that in Example 1, except that in Example 1, 0.15 g of piperazine (1.7 mmoles; this is corresponding to 476 ppm in terms of a nitrogen atom content relative to 1-(2-t-butylphenyloxy)-2-butanol) and 0.75 g of triethylamine (7.4 mmoles; this is corresponding to 691 ppm in terms of a nitrogen atom content relative to 1-(2-t-butylphenyloxy)-2-butanol) as the raw material were added in place of the n-octylamine. The pH of the raw material mixture at the time of commencement of the reaction was found to be 9.9. Results are shown in Table 2.

Example 8

Production of 1-(2-t-butylcyclohexyloxy)-2-butanol

In a 500-mL autoclave, 150 g (675 mmoles) of 1-(2-t-butylphenyloxy)-2-butanol, 2.85 g of a 2% active carbon-supported palladium catalyst containing 1% of sodium in terms of a metal content, which was obtained by impregnating the catalyst in a sodium hydroxide aqueous solution (the sodium mass is corresponding to 190 ppm relative to 1-(2-t-butylphenyloxy)-2-butanol as the raw material, pH: 10.2) (palladium: 0.057 g), and 0.15 g of a 5% active carbon-supported ruthenium catalyst (pH: 7.8) (ruthenium: 0.0057 g) were added and allowed to react at a hydrogen pressure of 2.0 MPa and 190° C. for 7 hours. The pH of the raw material mixture at the time of commencement of the reaction was 8.8.

After termination of the reaction, the catalysts were filtered, and distillation was carried out to obtain 1-(2-t-butyl-cyclohexyloxy)-2-butanol. Results are shown in Table 2.

Comparative Example 3

Production of 1-(2-t-butylcyclohexyloxy)-2-butanol 1-(2-t-butylcyclohexyloxy)-2-butanol was obtained by carrying out the reaction in the same manner as that in Example 8, except that in Example 8, 2.85 g of a 2% active carbon-supported palladium catalyst (pH: 7.3) was used in place of 2.85 g of the 2% active carbon-supported palladium catalyst containing 1% of sodium; and the pH of the raw material mixture at the time of commencement of the reaction was changed to 6.8. Results are shown in Table 2.

Example 9

Production of 1-(2-t-butylcyclohexyloxy)-2-butanol 1-(2-t-butylcyclohexyloxy)-2-butanol was obtained by carrying out the reaction in the same manner as that in Example 1, except that in Example 1, a 2% active carbon-supported palladium catalyst (manufactured by N.E. Chemcat Corporation, pH: 9.8) was used in place of the 2% active carbon-supported palladium catalyst (manufactured by N.E. Chemcat Corporation, pH: 7.3); the n-octylamine was not used; and the pH of the raw material mixture at the time of commencement of the reaction was changed to 7.5. Results are shown in Table 2.

Example 10

Production of 1-(2-t-butylcyclohexyloxy)-2-propanol 1-(2-t-butylcyclohexyloxy)-2-propanol was obtained by carrying out the reaction in the same manner as that in Example 1, except that in Example 1, 150 g (720 mmoles) of 1-(2-t-butylphenyloxy)-2-propanol and 1.5 g of diisopropylamine (14.8 mmoles; this is corresponding to 1,400 ppm in terms of a nitrogen atom content relative to the raw material 1-(2-t-butylphenyloxy)-2-propanol) were used in place of the 1-(2-t-butylphenyloxy)-2-butanol and the n-octylamine, respectively; and the pH of the raw material mixture at the time of commencement of the reaction was changed to 9.5. Results are shown in Table 2.

Comparative Example 4

Production of 1-(2-t-butylcyclohexyloxy)-2-propanol 1-(2-t-butylcyclohexyloxy)-2-propanol was obtained by carrying out the reaction in the same manner as that in Example 10, except that in Example 10, the diisopropylamine was not added; and the pH of the raw material mixture at the time of commencement of the reaction was changed to 6.5. Results are shown in Table 2.

Example 11

Production of 1-(2-t-butylcyclohexyloxy)-2-propanol

In a 500-mL autoclave, 150 g (720 mmoles) of 1-(2-t-butylphenyloxy)-2-propanol, 2.85 g of a 2% active carbon-supported palladium catalyst (palladium: 0.057 g) (manufactured by N.E. Chemcat Corporation, pH: 7.3), 0.15 g of a 5% active carbon-supported ruthenium catalyst (ruthenium: 0.0057 g) (manufactured by N.E. Chemcat Corporation, pH: 7.2), and 0.01 g of potassium carbonate (this is corresponding to 38 ppm in terms of a potassium metal relative to 1-(2-t-butylphenyloxy)-2-propanol) as the raw material were added and allowed to react at a hydrogen pressure of 2.0 MPa and 190° C. for 7 hours. The pH of the raw material mixture at the time of commencement of the reaction was 7.8.

After termination of the reaction, the catalysts were filtered, and distillation was carried out to obtain 1-(2-t-butyl-cyclohexyloxy)-2-propanol. Results are shown in Table 2.

Test Example

With respect to the 1-(2-t-butylcyclohexyloxy)-2-alkanols obtained in Examples 1 to 11 and Comparative Examples 1 to 4, the fragrance notes were evaluated by the following method. Results are shown in Tables 1 and 2.

<Evaluation Method of Fragrance Notes>

The fragrance notes were evaluated by plural expert panelists. The fragrance was enumerated in the order from one the sample which was felt stronger. With respect to the evaluation sample having a characteristic in the fragrance notes, its decision was also added. The overall evaluation was ranked according to the following criteria.

A: The evaluation sample is extremely interesting, and its value as a perfume material is high.

B: The evaluation sample has a sufficient value as a perfume material.

C: The evaluation sample has substantially sufficient value as a perfume material.

D: The evaluation sample has a slightly low value as a perfume material.

<Evaluation Method of Persistence of Aroma>

The evaluation sample was attached to a fragrance testing paper and evaluated on how many days the fragrance stayed by plural expert panelists.

TABLE 1

|  |  | Example 1 | Example 2 | Comparative Example 1 | Example 3 | Comparative Example 2 | Example 4 | Example 5 | Example 6 |
|---|---|---|---|---|---|---|---|---|---|
| Reaction condition | | | | | | | | | |
| $R^1$ | Type | Ethyl | Ethyl | Ethyl | Ethyl | Ethyl | Ethyl | Ethyl | Ethyl |
| Solvent | *1 | No | No | No | isoPrOH | isoPrOH | isoPrOH | isoPrOH | isoPrOH |
| Palladium catalyst (A) | pH | 7.3 | 7.9 | 7.3 | 7.3 | 7.3 | 7.6 | 8.5 | 9.2 |
| Metal catalyst (B) | Type | Ruthenium | Ruthenium | Ruthenium | Ruthenium | Ruthenium | Ruthenium | Ruthenium | Ruthenium |
|  | pH | 7.2 | 7.2 | 7.2 | 7.2 | 7.2 | 7.2 | 7.2 | 7.2 |
| Basic substance | Type | Octylamine | Octylamine | — | Morpholine | — | — | — | — |
|  | ppm *2 | 1100 | 1100 |  | 322 |  |  |  |  |
| pH of raw material mixture | | 9.2 | 9.9 | 6.8 | 7.5 | 7.3 | 7.5 | 8.3 | 8.9 |
| Results | | | | | | | | | |
| Yield | [%] | 78 | 82 | 75 | 77 | 73 | 83 | 84 | 81 |
| Ratio of trans-isomer | [%] *3 | 46 | 46 | 39 | 45 | 37 | 45 | 45 | 45 |
| Evaluation | | | | | | | | | |
| Fragrance notes | | Strongly amber-like Woody Slightly camphor-like | Strongly amber-like Woody Slightly camphor-like | Amber-like Woody Slightly camphor-like Slightly straw-like | Strongly amber-like Woody Slightly camphor-like | Amber-like Woody Slightly camphor-like | Amber-like Woody Slightly camphor-like | Amber-like Woody Slightly camphor-like | Amber-like Woody Slightly camphor-like |
| Decision | | Sweet and voluminous | Sweet and voluminous | — | Sweet and voluminous | Slightly light in scent | Sweet and voluminous | Sweet and voluminous | Sweet and voluminous |
| Overall evaluation | | A | A | C | A | D | A | A | A |
| Persistence of aroma (days) | | 6 | 6 | 4 | 6 | 4 | 6 | 6 | 6 |

*1: isoPrOH: Isopropyl alcohol
*2: Addition amount (ppm) in terms of a nitrogen atom content relative to [1-(2-butylphenyloxy)-2-butanol] as the raw material
*3: Proportion of the trans-isomer of the product [1-(2-t-butylcyclohexyloxy)-2-butanol]

TABLE 2

|  |  | Example 1 | Example 7 | Example 8 | Comparative Example 3 | Example 9 | Example 10 | Comparative Example 4 | Example 11 |
|---|---|---|---|---|---|---|---|---|---|
| Reaction condition | | | | | | | | | |
| $R^1$ | Type | Ethyl | Ethyl | Ethyl | Ethyl | Ethyl | Methyl | Methyl | Methyl |
| Solvent | | No | No | No | No | No | No | No | No |
| Palladium catalyst (A) | pH | 7.3 | 7.3 | 10.2 *2 | 7.3 | 9.8 | 7.3 | 7.3 | 7.3 |
| Metal catalyst (B) | Type | Ruthenium | Ruthenium | Ruthenium | Ruthenium | Ruthenium | Ruthenium | Ruthenium | Ruthenium |
|  | pH | 7.2 | 7.2 | 7.8 | 7.8 | 7.2 | 7.2 | 7.2 | 7.2 |
| Basic substance | Type | Octylamine | Piperazine/ triethylamine | Sodium hydroxide | — | — | Diisopropyl- amine | — | Potassium carbonate |
|  | ppm *1 | 1100 | 476/691 | 190 |  |  | 1400 |  | 38 |
| pH of raw material mixture | | 9.2 | 9.9 | 8.8 | 6.8 | 7.5 | 9.5 | 6.5 | 7.8 |

TABLE 2-continued

|  |  | Example 1 | Example 7 | Example 8 | Comparative Example 3 | Example 9 | Example 10 | Comparative Example 4 | Example 11 |
|---|---|---|---|---|---|---|---|---|---|
| Results |  |  |  |  |  |  |  |  |  |
| Yield | [%] | 78 | 82 | 79 | 75 | 83 | 83 | 75 | 79 |
| Ratio of trans-isomer | [%] *3 | 46 | 49 | 45 | 40 | 45 | 45 | 38 | 45 |
| Evaluation |  |  |  |  |  |  |  |  |  |
| Fragrance notes |  | Strongly amber-like Woody Slightly camphor-like | Strongly amber-like Woody Slightly camphor-like | Strongly amber-like Woody Slightly camphor-like Slightly straw-like | Amber-like Woody Slightly camphor-like Slightly soil-like | Strongly amber-like Woody Slightly camphor-like | Strongly amber-like Woody Camphor-like | Amber-like Woody Slightly mint-like | Strongly amber-like Woody Camphor-like |
| Decision |  | Sweet and voluminous | Sweet and voluminous | Sweet and voluminous | — | Slightly light in scent | — | — | — |
| Overall evaluation |  | A | A | A | C | A | B | C | B |
| Persistence of aroma (days) |  | 6 | 6 | 6 | 4 | 6 | 3 | 2 | 3 |

*1: Addition amount (ppm) in terms of a nitrogen atom content relative to [1-(2-t-butylphenyloxy)-2-butanol] as the raw material
*2: pH after impregnation with sodium hydroxide
*3: Proportion of the trans-isomer of the product [1-(2-t-butylcyclohexyloxy)-2-butanol or the like]

Formulating Example

To 920 parts by mass of a floral oriental-note formulated perfume having the following composition, 80 parts by mass of the perfume composition of the present invention obtained in Example 11. As a result, the powdery sweetness was strengthened.

<Composition of floral oriental-note formulated perfume>

| Bergamot oil: | 80 parts by mass |
|---|---|
| Dihydromyrcenol: | 25 parts by mass |
| Allyl-2-pentyloxyglycolate: | 5 parts by mass |
| Methyl phenyl carbinyl acetate: | 10 parts by mass |
| Ylang-ylang base: | 50 parts by mass |
| Rose base: | 50 parts by mass |
| Jasmine base: | 100 parts by mass |
| Methyl dihydrojasmonate: | 130 parts by mass |
| Methyl ionone gamma: | 150 parts by mass |
| SANDALMYSORE CORE *1: | 50 parts by mass |
| TONALIDE *2: | 100 parts by mass |
| Benzyl salicylate: | 50 parts by mass |
| Coumarin: | 50 parts by mass |
| Vanillin: | 20 parts by mass |
| Amber base: | 50 parts by mass |
|  | 920 parts by mass |

(Note)
*1: 2-Methyl-4-(2,3,3-trimethyl-3-cyclopentyn-1-yl)-2-buten-1-ol, manufactured by Kao Corporation
*2: 7-Acetyl-1,1,3,4,4,6-hexamethyltetrahydronaphthalene, manufactured by PFW Aroma Chemicals B.V.

INDUSTRIAL APPLICABILITY

According to the production method of the present invention, a 1-(2-t-butylcyclohexyloxy)-2-alkanol having a high trans-isomer content and a strong woody or amber-like fragrance as a perfume material and also having excellent persistence of aroma can be efficiently produced. The produced 1-(2-t-butylcyclohexyloxy)-2-alkanol can be used as a perfume material for an aromatizing component of, for example, soaps, shampoos, conditioners, detergents, toiletries, spray products, aromatics, perfumeries, bath salts, etc.

The invention claimed is:

1. A method of producing a 1-(2-t-butylcyclohexyloxy)-2-alkanol, comprising:

adjusting a raw material mixture comprising a 1-(2-t-butylphenyloxy)-2-alkanol represented by formula (1)

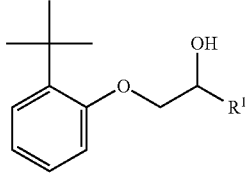

(1)

to a pH of from 7.5 to 10.0; and hydrogenating said 1-(2-t-butylphenyloxy)-2-alkanol represented by formula (1) in the presence of a palladium catalyst (A) and a metal catalyst (B) comprising at least one member selected from the group consisting of ruthenium, rhodium, platinum, and nickel, wherein $R^1$ is a methyl group or an ethyl group.

2. The method of producing a 1-(2-t-butylcyclohexyloxy)-2-alkanol according to claim 1, wherein, during said hydrogenating, a basic substance is added in the raw material mixture.

3. The method of producing a 1-(2-t-butylcyclohexyloxy)-2-alkanol according to claim 2, wherein the basic substance is at least one member selected from the group consisting of an amine, an alkali metal compound, and an alkaline earth metal compound.

4. The method of producing a 1-(2-t-butylcyclohexyloxy)-2-alkanol according to claim 2, wherein the addition amount of the basic substance is from 1 to 3,000 ppm in terms of a nitrogen atom content or a metal content relative to the 1-(2-t-butylphenyloxy)-2-alkanol represented by the formula (1).

5. The method of producing a 1-(2-t-butylcyclohexyloxy)-2-alkanol according to claim 3, wherein the amine is at least one member selected from the group consisting of ammonia, a monovalent primary amine, a monovalent secondary amine, a monovalent tertiary amine, and a polyvalent amine.

6. The method of producing a 1-(2-t-butylcyclohexyloxy)-2-alkanol according to claim 3, wherein the addition amount of the amine is from 100 to 3,000 ppm in terms of a nitrogen atom content relative to the 1-(2-t-butylphenyloxy)-2-alkanol represented by formula (1).

7. The method of producing a 1-(2-t-butylcyclohexyloxy)-2-alkanol according to claim 3, wherein the addition amount of the alkali metal compound or the alkaline earth metal compound is from 1 to 1,000 ppm in terms of a metal content relative to the 1-(2-t-butylphenyloxy)-2-alkanol represented by the formula (1).

8. The method of producing a 1-(2-t-butylcyclohexyloxy)-2-alkanol according to claim 1, wherein a mass ratio of palladium in the palladium catalyst (A) and at least one of ruthenium, rhodium, platinum, and nickel in the metal catalyst (B), [(A)/(B)], is from 80/20 to 99/1.

9. The method of producing a 1-(2-t-butylcyclohexyloxy)-2-alkanol according to claim 1, wherein the amount of an organic solvent in said hydrogenating is not more than 10% by mass relative to the 1-(2-t-butylphenyloxy)-2-alkanol.

10. The method of producing a 1-(2-t-butylcyclohexyloxy)-2-alkanol according to claim 9, wherein the amount of the organic solvent in said hydrogenating is 0% by mass relative to the 1-(2-t-butylphenyloxy)-2-alkanol.

11. The method of producing a 1-(2-t-butylcyclohexyloxy)-2-alkanol according to claim 1, wherein the content of a trans-isomer of the 1-(2-t-butylcyclohexyloxy)-2-alkanol is 41% by mass or more.

12. The method of producing a 1-(2-t-butylcyclohexyloxy)-2-alkanol according to claim 1, wherein $R^1$ in formula (1) represents an ethyl group.

13. The method of producing a 1-(2-t-butylcyclohexyloxy)-2-alkanol according to claim 1, wherein the palladium catalyst (A) is a supported catalyst supported on a carrier.

14. The method of producing a 1-(2-t-butylcyclohexyloxy)-2-alkanol according to claim 13, wherein the carrier of the palladium catalyst (A) is an inorganic carrier.

15. The method of producing a 1-(2-t-butylcyclohexyloxy)-2-alkanol according to claim 1, wherein the pH of the palladium catalyst (A) is 7.0 or more and not more than 12.0.

16. The method of producing a 1-(2-t-butylcyclohexyloxy)-2-alkanol according to claim 1, wherein the metal catalyst (B) is a supported catalyst supported on a carrier.

17. The method of producing a 1-(2-t-butylcyclohexyloxy)-2-alkanol according to claim 1, wherein the pH of the metal catalyst (B) is 6.0 or more and not more than 12.0.

18. The method of producing a 1-(2-t-butylcyclohexyloxy)-2-alkanol according to claim 1, wherein a total amount of the palladium catalyst (A) and the metal catalyst (B) is 0.01% by mass or more and not more than 10% by mass relative to the 1-(24-butylphenyloxy)-2-alkanol represented by formula (1).

19. The method of producing a 1-(2-t-butylcyclohexyloxy)-2-alkanol according to claim 1, wherein a hydrogen pressure in said hydrogenating is 0.1 MPa or more and not more than 15 MPa.

20. The method of producing a 1-(2-t-butylcyclohexyloxy)-2-alkanol according to claim 1, wherein a reaction temperature during said hydrogenating is 50° C. or higher and not higher than 300° C.

* * * * *